(12) United States Patent
Hansen

(10) Patent No.: US 11,013,905 B2
(45) Date of Patent: May 25, 2021

(54) THERMAL INTERCONNECT FOR IMPLANTABLE BLOOD PUMP

(71) Applicant: TC1 LLC, St. Paul, MN (US)

(72) Inventor: John Freddy Hansen, Pleasanton, CA (US)

(73) Assignee: TCI LLC, St. Paul, MN (US)

( * ) Notice: Subject to any disclaimer, the term of this patent is extended or adjusted under 35 U.S.C. 154(b) by 189 days.

(21) Appl. No.: 15/976,719

(22) Filed: May 10, 2018

(65) Prior Publication Data

US 2018/0326133 A1 Nov. 15, 2018

Related U.S. Application Data

(60) Provisional application No. 62/505,020, filed on May 11, 2017.

(51) Int. Cl.

| | |
|---|---|
| *A61M 1/00* | (2006.01) |
| *A61M 60/148* | (2021.01) |
| *A61M 60/50* | (2021.01) |
| *A61M 60/82* | (2021.01) |
| *A61M 60/205* | (2021.01) |
| *A61M 60/419* | (2021.01) |

(52) U.S. Cl.
CPC ........ *A61M 60/148* (2021.01); *A61M 60/205* (2021.01); *A61M 60/419* (2021.01); *A61M 60/50* (2021.01); *A61M 60/82* (2021.01); *A61M 2205/3372* (2013.01); *A61M 2205/3606* (2013.01)

(58) Field of Classification Search
USPC ............................................ 600/16; 415/203
See application file for complete search history.

(56) References Cited

U.S. PATENT DOCUMENTS

| | | | | |
|---|---|---|---|---|
| 2002/0009363 | A1* | 1/2002 | Ozaki | F02K 7/06 415/203 |
| 2003/0163019 | A1 | 8/2003 | Goldowsky | |
| 2004/0210289 | A1* | 10/2004 | Wang | A61K 9/5094 607/116 |
| 2006/0287697 | A1* | 12/2006 | Lennox | A61F 7/0085 607/96 |

FOREIGN PATENT DOCUMENTS

| | | |
|---|---|---|
| WO | 2010036815 A2 | 4/2010 |
| WO | 2012024493 A1 | 2/2012 |
| WO | 2014165635 A2 | 10/2014 |

* cited by examiner

*Primary Examiner* — Nicole F Lavert
*Assistant Examiner* — Nicole F Johnson
(74) *Attorney, Agent, or Firm* — Kilpatrick Townsend & Stockton LLP

(57) ABSTRACT

Systems, methods, and devices for improved cooling of an implantable blood pump are disclosed herein. The implantable blood pump can include: a pump housing defining an internal volume and including a wall defining a blood flow conduit extending through the pump housing; a rotor including a magnet and located within the blood flow conduit; a magnetic core located in the internal volume and extending circumferentially around the blood flow conduit and the rotor, which magnetic core terminates proximate to the wall; a controller located in the internal volume; and a thermal conductor contacting and preferentially thermally connecting the controller and the magnetic core, wherein the thermal conductor is electrically non-conductive.

13 Claims, 12 Drawing Sheets

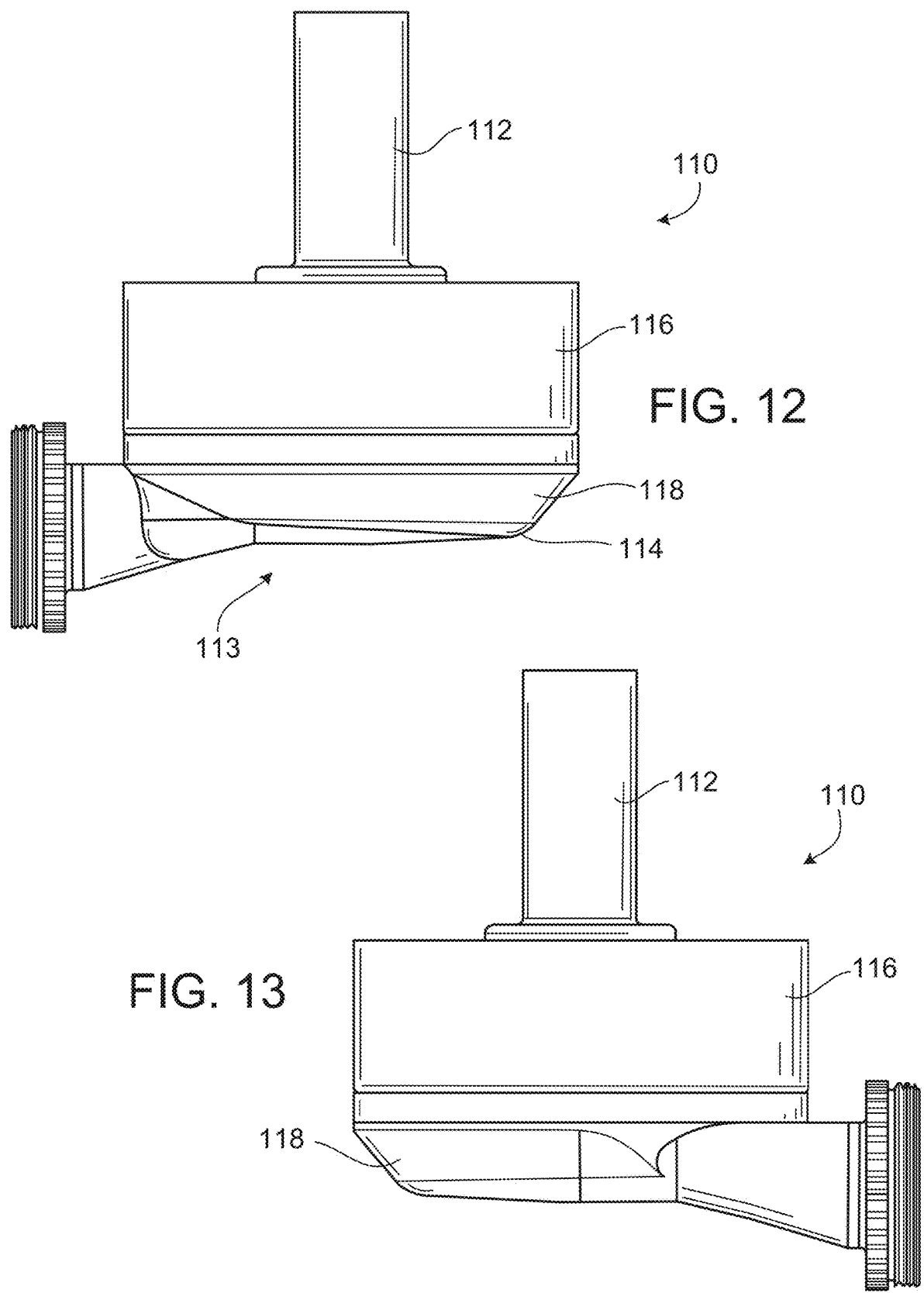

THERMAL INTERCONNECT FOR IMPLANTABLE BLOOD PUMP

CROSS-REFERENCE TO RELATED APPLICATIONS

The present application claims the benefit of U.S. Provisional Application Ser. No. 62/505,020, filed on May 11, 2017, which is incorporated by reference herein in its entirety for all purposes.

BACKGROUND

This application relates generally to mechanical circulatory support systems, and more specifically relates to control systems, for an implantable blood pump Ventricular assist devices, known as VADs, are implantable blood pumps used for both short-term (i.e., days, months) and long-term applications (i.e., years or a lifetime) where a patient's heart is incapable of providing adequate circulation, commonly referred to as heart failure or congestive heart failure. According to the American Heart Association, more than five million Americans are living with heart failure, with about 670,000 new cases diagnosed every year. People with heart failure often have shortness of breath and fatigue. Years of living with blocked arteries or high blood pressure can leave your heart too weak to pump enough blood to your body. As symptoms worsen, advanced heart failure develops.

A patient suffering from heart failure, also called congestive heart failure (CHF), may use a VAD while awaiting a heart transplant or as a long term destination therapy. In another example, a patient may use a VAD while recovering from heart surgery. Thus, a VAD can supplement a weak heart (i.e., partial support) or can effectively replace the natural heart's function. VADs can be implanted in the patient's body and powered by an electrical power source inside or outside the patient's body.

Due to VAD workload in constantly pumping blood, VADs can have significantly higher power requirements than other types of implantable devices such as pacemakers or other stimulators. Because of these power requirements, VADs can be externally powered by delivering power from outside of a patient's body to the VAD inside of the patient's body. Further, because of these higher power requirements, VADs generate significant amounts of heat during operation.

In spite of the obvious benefits of VAD therapy, there remains a need to improve the therapy and design of VADs in particular. One aim for improving VADs is to provide smaller pumps with the same or better performance. A challenge with smaller pumps is management of heat generated in the pump. Generally smaller pumps need to be designed to rotate the impeller at the same or even a higher rotational speed, yet they have a smaller surface area in contact with adjacent tissue. This can translate to greater localized heating which can lead to tissue damage. In certain cases regulatory requirements for such tissue heating can be a limiting factor on performance. Accordingly, further VAD improvements, and particularly improvements to heat management within VADs are desired.

BRIEF SUMMARY

Embodiments of the present disclosure relate to devices, systems, and methods for efficiently managing heat within a ventricular assist system, and in certain respects an implantable blood pump. This can include the generation of a preferential conductive heat pathway connecting electronics within the blood pump to a portion of a blood conduit extending through a housing of the blood pump. This preferential conductive heat pathway can be generated by the conductive, thermal connection of the electronics with a stator of the blood pump, and specifically with a back iron of the stator or with one or several poles of the stator. While this preferred thermal conductive pathway may be longer than other conductive pathways from the electronics to a surface of the blood pump, it is of advantage as significant heat transfer along this thermal conductive pathway can be achieved. Further, the relatively higher thermal conductivity of the components forming this preferred thermal conductive pathway, than other components of the blood pump such as the potting material encompassing the stator and the electronics, allows for improved heat management that minimizes localized heating, hot spots, and/or tissue damage to the patient.

One aspect of the present disclosure relates to an implantable blood pump. The implantable blood pump includes a pump housing having a wall defining a blood flow conduit extending through the pump housing and an internal volume; a rotor including a magnet and disposed within the blood flow conduit; a magnetic core disposed in the internal volume and extending circumferentially around the blood flow conduit and the rotor, which magnetic core terminates proximate to the wall; a controller disposed in the internal volume; and a continuous thermal pathway extending through the magnetic core between the controller and the wall for transferring heat to blood transiting the blood flow conduit.

In some embodiments, a thermal conductor thermally couples the controller to the magnetic core so as to provide a desired path of least resistance for heat flow generated by the blood pump to blood transitioning the blood flow conduit. In some embodiments, the thermal conductor can be a thermal interface material. In some embodiments, the thermal interface material can be a thermal conductive pad or thermal grease. In some embodiments, the implantable blood pump includes potting material surrounding the magnetic core and the controller. In some embodiments, the potting material isotropically transfers heat from the controller. In some embodiments, the thermal conductor has higher thermally conductivity than the potting material.

In some embodiments, the magnetic core is thermally coupled to blood passing through and/or transiting the blood flow conduit via the wall defining the blood flow conduit. In some embodiments, the blood flow conduit includes an entrance and an exit, and the controller is positioned relatively proximate to the entrance of the blood flow conduit than the magnetic core. In some embodiments, the magnetic core can include a plurality of L-shaped pole pieces. In some embodiments, the thermal conductor is electrically nonconductive.

In some embodiments, a thermal conductor thermally couples the controller to the magnetic core. In some embodiments, the continuous thermal pathway extends from the electronics through the thermal conductor and the magnetic core. In some embodiments, the heat flow is generated by at least one of: the controller; or the magnetic core. In some embodiments, the magnetic core includes a plurality of pole pieces arranged circumferentially around the blood flow conduit. In some embodiments, each of the pole pieces includes a first leg extending along the blood flow conduit and a second leg that extends towards the wall. In some embodiments, an end of each of the second legs is separated from the wall by a gap of between 0.05 mm and 2 mm.

In some embodiments, a thermal conductor thermally couples the controller to the magnetic core. In some embodiments, the thermal conductor contacts the magnetic core via at least one of the pole pieces. In some embodiments, the magnetic core includes a back iron, and the thermal conductor contacts the magnetic core via the back iron. In some embodiments, the controller and the magnetic core are embedded in a potting material. In some embodiments, the thermal conductor extends through the potting material and thermally connects the controller and the magnetic core. In some embodiments, the potting material can be epoxy. In some embodiments, the epoxy has isotropic thermal conductivity.

One aspect of the present disclosure relates to a method of assisting blood circulation in a patient using an implantable blood pump having a housing having an internal volume and interior wall defining a blood flow conduit, a rotor disposed within the blood flow conduit, a motor stator disposed in the internal volume, a controller disposed in the internal volume, and a thermal conductor thermally coupling the controller to the motor stator. The method can include: drawing a flow of blood from a patient's heart into the blood flow conduit formed by the interior wall of the blood pump housing; passing the flow of blood through the motor stator disposed within the housing and the rotor disposed within the blood flow conduit, which heat flow is conducted from the controller to the blood pumped through the blood flow conduit via the motor stator; and outputting the flow of blood from the blood flow conduit to an aorta of the patient.

In some embodiments the method includes, controlling rotation of the rotor within the blood flow conduit. In some embodiments, the thermal conductor is electrically non-conductive. In some embodiments, the thermal conductor includes a thermal interface material. In some embodiments the thermal interface material includes a thermal conductive pad or thermal grease. In some embodiments, a thermal zone is adjacent to the motor stator. In some embodiments, the thermal conductor provides a desired path of least resistance for heat flow from the controller to a portion of the interior wall.

In some embodiments the method includes, passing the flow of blood through a volute between the motor stator and a controller, and through a thermal zone heated by the controller. In some embodiments the thermal zone is adjacent to the controller. In some embodiments, the motor stator includes a plurality of stator poles arranged circumferentially around the blood flow conduit. In some embodiments, each of the motor stator poles includes a first leg extending along the blood flow conduit and a second leg that extends towards the interior wall. In some embodiments, the motor stator is contained within a first internal compartment of the housing and the controller is contained with a second internal compartment of the housing. In some embodiments, the motor stator and the controller are each potted.

One aspect of the present disclosure relates to an implantable blood pump. The implantable blood pump includes: a pump housing having an exterior wall and an interior wall, wherein the exterior wall and the interior wall together define an internal volume, and wherein the interior wall defines a blood flow conduit extending through the pump housing; a controller disposed in the internal volume; a first conductive heat transfer pathway thermally coupling the controller with the exterior wall and the interior wall; and a second conductive heat transfer pathway thermally coupling the controller with a portion of the interior wall.

In some embodiments, the second conductive heat transfer pathway includes a thermal conductor thermally coupling the controller to the blood flow conduit via the portion of the interior wall. In some embodiments, the second conductive heat transfer pathway includes a magnetic core thermally coupling the thermal conductor.

The preceding presents a simplified summary of some embodiments of the invention in order to provide a basic understanding of the invention. This summary is not an extensive overview of the invention. It is not intended to identify key/critical elements of the invention or to delineate the scope of the invention. Its sole purpose is to present some embodiments of the invention in a simplified form as a prelude to the more detailed description that is presented later. For a fuller understanding of the nature and advantages of the present invention, reference should be made to the ensuing detailed description and accompanying drawings.

BRIEF DESCRIPTION OF THE DRAWINGS

FIG. 12 is a right side view of the blood pump of FIG. 8.

FIG. 13 is a left side view of the blood pump of FIG. 8.

DETAILED DESCRIPTION

Figure 1:
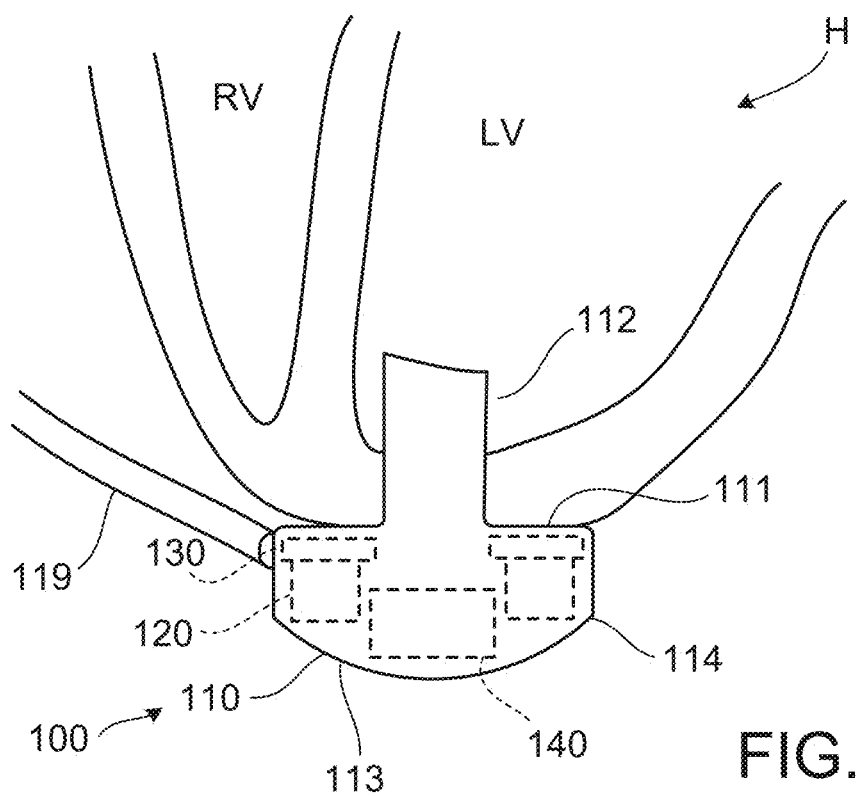
FIG. 1 is an illustration of a blood pump in a use position implanted in a patient's body.

Heat management within implantable devices such as VADs presents unique problems as compared to heat management within other consumer devices because they are implanted within the body. The implanted environment makes it harder to remove heat from the device without risking injury to the patient. Indeed, many countries have implemented strict regulatory requirements for tissue heating, such as, a maximum temperature rise of one or two degrees in any section of adjacent tissue. As a result of these clinical and regulatory issues, VADs are limited to surface temperatures far below temperatures viewed as acceptable in other electronic products (e.g., no more than 1° C. rise in local tissue temperature). In addition to this, by virtue of operating inside of a human body and tissue sensitivity to temperature, a large temperature gradient is not maintained between external surfaces of a VAD and the tissue in which the VAD is embedded. The implanted environment also makes it challenging to employ typical heat management techniques because the device form factor needs to be small. Further, because much of the tissue surrounding the VAD is static and tissue is a poor thermal conductor, there is a risk of localized hot spots in the tissue.

As VADs become more complex, smaller, and/or more computer-controlled, greater amounts of heat are generated by the VAD and thus greater amounts of heat need to be dissipated without increasing surface temperatures in violations of regulatory requirements or to the detriment of the patient. This is particularly seen in implantable blood pumps as more processing power and more control is located at the implantable blood pump in the form of an increased number of heat generating electrical components. The issue of heat management in the implantable blood pump is further complicated by steps taken to protect portions of the implantable blood pump from the in vivo environment. Specifically, electronics and components of the motor of the implantable blood pump are frequently potted within a potting material. Because of the need to seal these potted components, heat exchangers or heat sinks extending from inside the potting to outside of the potting may not be feasible.

Embodiments disclosed herein address these heat management problems via the preferential transfer of heat to a portion of blood conduit which is a part of the implantable blood pump that channels moving blood. Certain embodiments make use of the fact that moving blood is a heat sink and provides advantages over the use of tissue surrounding the implantable blood pump. For one, blood flows throughout the body and can carry away received heat energy. Certain aspects of the invention are directed to features for improving the design of the pump to direct heat to the moving blood and away from tissue. To effectively carry heat to the portion of the blood conduit a conductive heat transfer pathway through the implantable blood pump may be created to preferentially transfer heat to the blood conduit.

The preferential transfer of heat to the blood conduit can be accomplished by channeling heat from heat generating components directly towards the blood conduit or by channeling heat indirectly from the heat generating components towards the blood conduit. While the direct channeling of heat to the blood conduit can be more efficient, it can increase risk of failure of the potting and complicate design of the blood pump. Although indirectly channeling heat to the blood conduit may appear inefficient due to the larger length of this heat transfer pathway as compared to the heat transfer pathway used to directly channel heat to the blood conduit, incorporating pre-existing structures of the blood pump into the heat transfer pathway can avoid complex changes to the design of the blood pump and increased risks of compromising the potting. Thus, the transfer of heat through a longer heat transfer pathway can provide significant benefit over the transfer of heat through shorter heat transfer pathways. Specifically, such a heat transfer pathway can reduce surface temperatures of the implantable blood pump by at least 0.5° C., by at least 0.8° C., by at least 1.1° C., or any other or intermediate temperature. Specific embodiments of the implantable blood pump for improved heat management are disclosed below.

With reference to FIGS. 1 and 8-15, an exemplary left ventricular assist blood pump 100 having a puck-shaped housing 110 is implanted in a patient's body with a first face 111 of the housing 110 positioned against the patient's heart H and a second face 113 of the housing 110 facing away from the heart H. The first face 111 of the housing 110 includes an inlet cannula 112 extending into the left ventricle LV of the heart H. The second face 113 of the housing 110 has a chamfered edge 114 to avoid irritating other tissue that may come into contact with the blood pump 100, such as the patient's diaphragm. In one embodiment, the illustrated puck-shaped housing 110 includes a stator 120, also referred to herein as the magnetic core 120 or the core 120, and electronics 130, also referred to herein as control electronics 130 or controller 130, of the pump 100 positioned on the inflow side of the housing toward first face 111, and a rotor 140 of the pump 100 is positioned along the second face 113. The stator 120 can include pole pieces 123a-123f and windings 126 that can include, for example, a drive coil 125 and a levitation coil 127. The drive coil 125 can generate an electromagnetic field for creating a torque at the rotor 140 to cause the rotor 140 to rotate. The levitation coils 127 can generate an electromagnetic field to control the radial position of the rotor 140. In some embodiments, one or both of the drive coil 125 and the levitation coil 127 can be sources of heat.

In such embodiments, the electronics 130 are positioned between the stator 120 and the first face 111 and the stator 120 is positioned between the electronics 130 and the second face 113. This positioning of the stator 120, electronics 130, and rotor 140 permits the edge 114 to be chamfered along the contour of the rotor 140, as illustrated in at least FIGS. 2, 4, and 8-11, for example. In another embodiment, the puck-shaped housing 110 includes the stator 120 of the pump 100 positioned on the inflow side of the housing toward the first face 111, the electronics 130 of the pumps 100 positioned on the outflow side of the housing toward the second face 113.

The blood pump 100 can generate heat during operation, which heat can increase, among other things, the surface temperatures of all or portions of the blood pump 100. In some embodiments, for example, this heat can be generated by losses and/or inefficiencies in the blood pump 100. In some embodiments, for example, the blood pump 100 can have an efficiency such as a hydraulic efficiency of: less than 0.8, less than 0.7, less than 0.6, less than 0.5, less than 0.4, less than 0.3, less than 0.2, between approximately 0.2 and 0.6, between approximately 0.3 and 0.5, of approximately 0.3, of approximately 0.38, of approximately 0.4, of approximately 0.42, of approximately 0.5, or any other or intermediate value. In some embodiments, the blood pump can consume less than 50 W, less than 40 W, less than 30 W, less than 20 W, less than 10 W, less than 5 W, between approximately 1 W and 10 W, between approximately 2 W and 7 W, or any other or intermediate amount of power.

In some embodiments, the power consumption of the blood pump 100 varies based on the flow-rate and/or pressure of the blood exiting the blood pump 100. In some embodiments, for example, with a fluid having a viscosity of approximate 2.7 cP, or between approximately 1 cP and 4 cP, at a flow rate of between approximately 1 and 3 liters per minute (Lpm) or at approximately 2 Lpm, and at a pressure of between approximately 15 and 55 mmHG, or of approximately 35 mmHG, the blood pump 100 can consume approximately 1.9 W, which can include approximately 1 W of power consumed by the electronics 130, approximately 0.4 W of bearing losses, approximately 0.1 W of drive losses, and approximately 0.42 W for the driving of the rotor 140. In some embodiments, for example, with a fluid having a viscosity of approximate 2.7 cP, or between approximately 1 cP and 4 cP, at a flow rate of between approximately 4 and 7 Lpm or at approximately 5.4 Lpm, and at a pressure of between approximately 50 and 90 mmHG, or of approximately 70 mmHG, the blood pump 100 can consume approximately 4.2 W, which can include approximately 1 W of power consumed by the electronics 130, approximately 0.5 W of bearing losses, approximately 0.65 W of drive losses, and approximately 2 W for the driving of the rotor 140. In some embodiments, for example, with a fluid having a viscosity of approximate 2.7 cP, or between approximately 1 cP and 4 cP, at a flow rate of between approximately 5 and 10 Lpm or at approximately 7 Lpm, and at a pressure of between approximately 70 and 130 mmHG, or of approximately 100 mmHG, the blood pump 100 can consume approximately 6.6 W, which can include approximately 1 W of power consumed by the electronics 130, approximately 0.5 W of bearing losses, approximately 0.1.4 W of drive losses, and approximately 3.71 W for the driving of the rotor 140.

Figure 2:
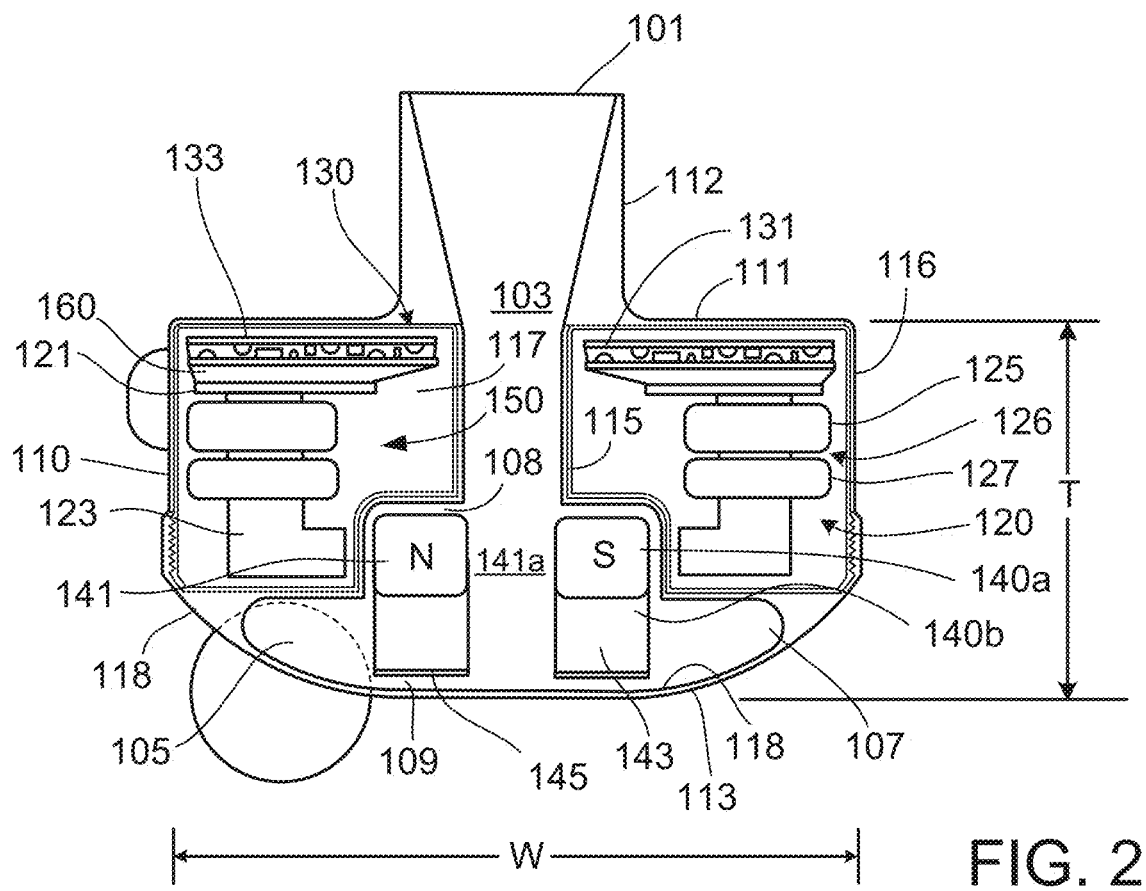
FIG. 2 is a cross-sectional view of the blood pump of FIG. 1.

Referring to FIG. 2 one layout of the blood pump 100 is shown. The blood pump 100, and specifically the housing 110 includes a dividing wall 115, also referred to herein as the interior wall 115, within the housing 110 defining a blood flow conduit 103. The blood flow conduit 103 extends from an inlet opening 101 of the inlet cannula 112 through the stator 120 to an outlet opening 105 defined by the housing 110. The rotor 140 is positioned within the blood flow conduit 103. The stator 120 is disposed circumferentially about a first portion 140a of the rotor 140, for example about a permanent magnet 141. The stator 120 is also positioned relative to the rotor 140 such that, in use, blood flows within the blood flow conduit 103 through the stator 120 before reaching the rotor 140. The permanent magnet 141 has a permanent magnetic north pole N and a permanent magnetic south pole S for combined active and passive magnetic levitation of the rotor 140 and for rotation of the rotor 140. The rotor 140 also has a second portion 140b that includes impeller blades 143. The impeller blades 143 are located within a volute 107 of the blood flow conduit such that the impeller blades 143 are located proximate to the second face 113 of the housing.

The puck-shaped housing 110 further includes a peripheral wall 116, also referred to herein as the exterior wall 116, that extends between the first face 111 and a removable cap 118. As illustrated, the peripheral wall 116 is formed as a hollow circular cylinder having a width W between opposing portions of the peripheral wall 116. The housing 110 also has a thickness T between the first face 111 and the second face 113 that is less than the width W. The thickness T is from about 0.5 inches to about 1.5 inches, and the width W is from about 1 inch to about 4 inches. For example, the width W can be approximately 2 inches, and the thickness T can be approximately 1 inch.

The peripheral wall 116 encloses an internal compartment 117 that surrounds the dividing wall 115 and the blood flow conduit 103. In some embodiments, the internal compartment 117 can contain the stator 120, the electronics 130, or the stator 120 and the electronics 130. The stator 120 and/or the electronics 130 can be disposed in the internal compartment 117 about the dividing wall 115. The stator 120 and the electronics 130 can, in some embodiments, be positioned adjacent to each other. In such embodiments, the stator 120 and the electronics 130 are physically and electrically separated so that the stator 120 does not short the electronics 130. In some embodiments, this separation between the stator 120 and the electronics 130 can be achieved via an air-gap, or the placement of a potting material between the stator 120 and the electronics.

The stator 120 and/or the electronics 130 located in the internal compartment 117 can be located in potting 150, and specifically can be located within a potting material that can fill some or all of any remaining portions of the internal compartment 117. This potting material can comprise a single potting material or multiple potting materials. The potting 150 can comprise any material fit for the environment and intended use, and can include, for example, a silicone or silicone compound, or an epoxy.

In some embodiments, the potting can be isotropic, and in other embodiments the potting 150 can be anisotropic. In some embodiments, for example, the potting 150 can comprise a first potting material have first properties covering a first portion of the stator 120 and/or the electronics 130 and the potting 150 can comprise a second potting material having second properties covering a second portion of the stator 120 and/or the electronics 130. Thus, in some embodiments, the potting 150 can have isotropic thermal conductivity and/or can isotropically transfer heat from the electronics 130, and in some embodiments, the potting 150 can have anisotropic thermal conductivity and/or anisotropically transfer heat from the electronics 130. In some embodiments, the potting material can have a thermal conductivity (k) of approximately: 0.1 W/(m*K); 0.26 W/(m*K); 0.5 W/(m*K); 0.75 W/(m*K); 1 W/(m*K); 2 W/(m*K); 3 W/(m*K); 5 W/(m*K); 10 W/(m*K); between 0.26 and 1 W/(m*K); or any other or intermediate value or range.

The stator 120 and the electronics 130 can, in some embodiments, be connected by a thermal conductor 160, which thermal conductor 16 can contact one or both of the stator 120 and the electronics 130. The thermal conductor 160 can, in some embodiments, additionally connect the circuit boards 131 and/or the components 133 to facilitate heat transfer throughout the electronics 130 and to the stator 120. The thermal conductor 160 can comprise a thermal interface material that can create a path for thermal conduction from the electronics 130 to the stator 120 that extends through the potting 150 as, in some embodiments, the thermal conductor 160 can extend through the potting 150. The thermal interface material can include, for example, a thermal conductive pad, thermal grease, thermal glue, thermal gap filler, or thermal adhesive. In some embodiments, the thermal conductor can comprise a thermal pad made of, for example, a silicone rubber having a thermal conductivity of, for example, approximately 17 W/(m*K).

The thermal conductor 160 can be electrically non-conductive, but can have thermal conductivity (k) that is higher than typical non-conductors, and in some embodiments significantly higher than the thermal conductivity of some or all of the potting 150. Thus, in some embodiments, the thermal conductivity of the thermal conductor 160 can be relatively higher than the thermal conductivity of the potting 150. In some embodiments, the thermal conductor 160 can have a thermal conductivity (k) or approximately: 5 W/(m*K); 10 W/(m*K); 15 W/(m*K); 17 W/(m*K); 20 W/(m*K); 25 W/(m*K); 30 W/(m*K); 50 W/(m*K); between 10 and 25 W/(m*K); or any other or intermediate value or range. Similarly, in some embodiments, one or both of: the back iron 121 and the pole pieces 123a-123f have thermal conductivity (k) that is higher, and in some embodiments significantly higher than the thermal conductivity of some or all of the potting 150. The thermal conductivity of the thermal conductor 160 and/or of one or both of the back iron 121 and the poles 123a-123f can be at least: 1.5 times; 2 times; 3 times; 4 times; 5 times; 6 times; 7 times; 8 times; 9 times; 10 times; 15 times; 20 times; 25 times; 50 times; 100 times; 500 times; 1000 times; or any other or intermediate multiple of the thermal conductivity of the potting 150. Due to this higher thermal conductivity of the thermal conductor 160, the thermal conductor preferentially thermally connects the electronics 130 and all or portions of the stator 120 such that heat flux through surfaces of the electronics 130 contacting the thermal conductor 160 is greater than heat flux through surfaces of the electronics 130 not contacting the thermal conductor 160.

In some embodiments all or portions of the stator 120 can have isotropic thermal conductivity, and in some embodiments, the stator 120 can have anisotropic thermal conductivity. In one embodiment, for example, all or portions of the stator can comprise a laminated material, and specifically, all or portions of the poles 123a-123f can be laminated. In such an embodiment, the laminations 124d of the poles 123a-123f can have an anisotropic thermal conductivity. Specifically, the thermal fast plane of the poles 123a-123f can be pointed inwards towards the blood conduit 103, and the thermally slow plane or axis can be pointed azimuthally or axially.

Figure 4:
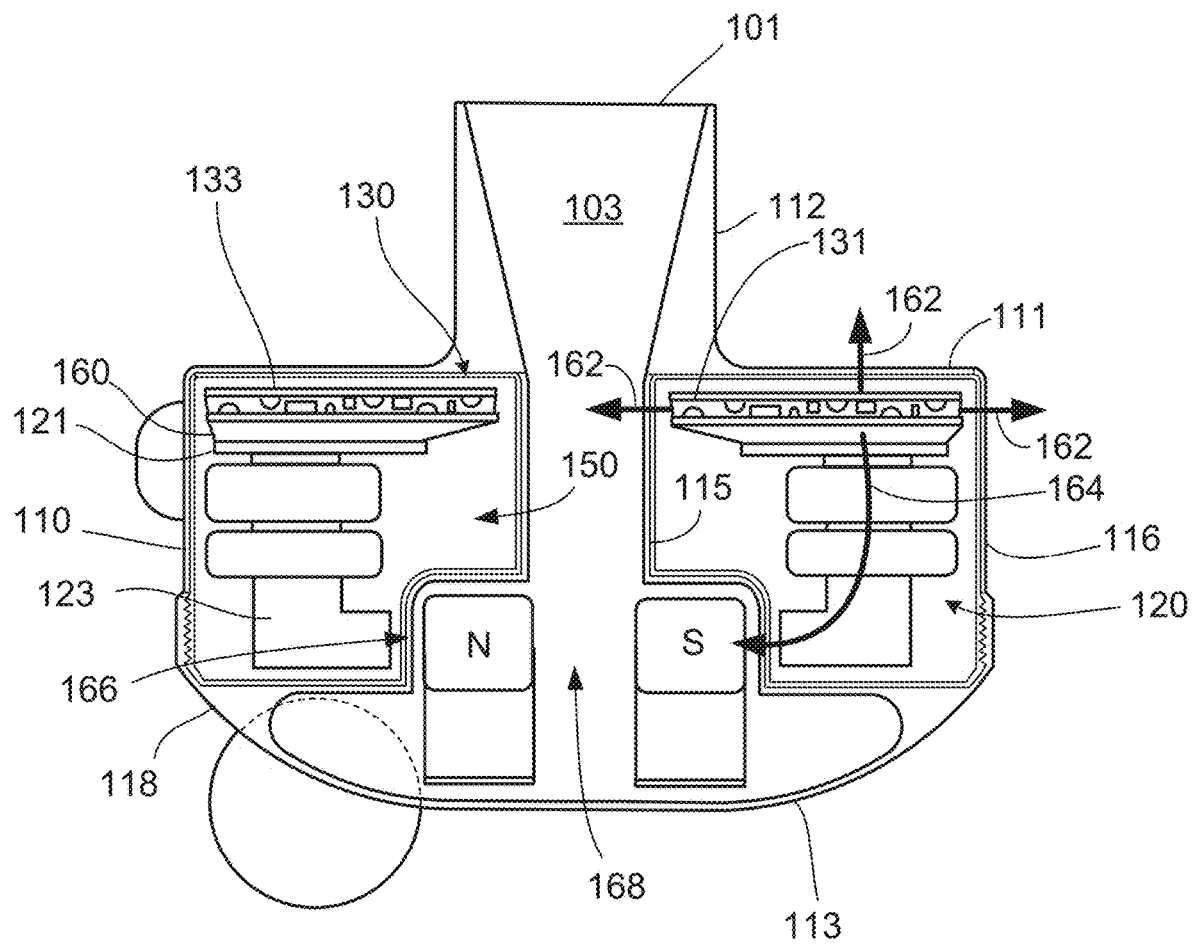
FIG. 4 is a cross-sectional view of one embodiment of the blood pump of FIG. 1 and conductive heat pathways.

As depicted in FIG. 4, the blood pump 100 can include multiple heat conduction pathways including a first conductive heat transfer pathway 162, also referred to herein as a first heat transfer pathway 162, and a second conductive heat transfer pathway 164, also referred to herein as a second heat transfer pathway 164. The first heat transfer pathway 162 is from the electronics 130 through the potting 150 surrounding the electronics 130. This first heat transfer pathway 162 extends in all directions from the electronics 130 in which the potting 150 contacts the electronics 130 and thermally connects the electronics 130 with the exterior wall 116 and/or the interior wall 115 of the blood pump 100.

The second heat transfer pathway 164 partially extends in the direction of blood flow through the blood flow conduit 103, or in other words partially extends along the blood flow conduit 103. Specifically, the second heat transfer pathway 164 is from the electronics 130 through the thermal conductor 160 and the stator 120, and terminates at a portion 166 of the interior wall 115 adjacent to an end 124c of the poles 123a-123f. This second heat transfer pathway 164 heats all or portions of the core 120 with heat from the electronics 130 or other components of the blood pump 100 thermally connected with the core 120. As seen in FIG. 4, the second heat transfer pathway 164 is longer than the first heat transfer pathway 162.

The portion 166 of the interior wall 115 circumferentially extends around the blood flow conduit 103 and defines a thermal zone 168 that is heated by the second heat transfer pathway 164. This thermal zone 168 is adjacent to the stator 120, and specifically is adjacent to the ends 124c of the poles 123a-123f. This thermal zone is preferentially heated by the second heat transfer pathway 164. In some embodiments, the temperature of the thermal zone complies with regulatory requirements and does not create pain, discomfort, or injury in the patient. In some embodiments, the blood in the blood flow conduit 103 is not heated to the point of causing pain, discomfort, or injury due to the flow of blood through the blood flow conduit 103.

The thermal conductivity of components I the second heat transfer pathway 164 can be higher than the thermal conductivity of components in the first heat transfer pathways 162. Specifically, the potting 150 can have a lower thermal conductivity than some or all of the components in the second heat transfer pathway 164. Thus, in some embodiments, the potting 150 can insulate portions of the housing 110, and specifically of the external surface 116 of the housing 110 to minimize heat transfer to those insulated portions and to thereby facilitate heat transfer via the second heat transfer pathway 164.

Figure 5:
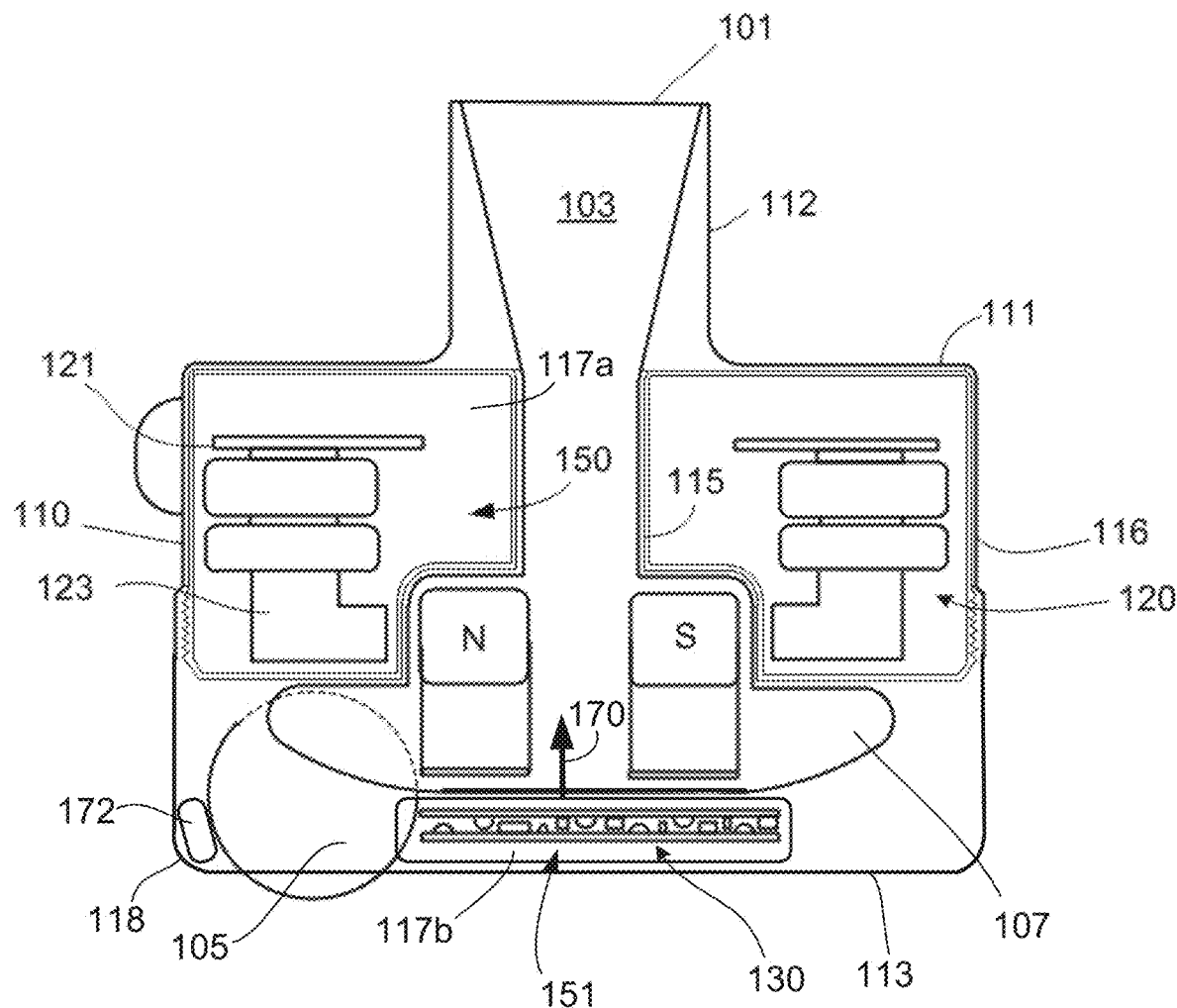
FIG. 5 is a cross-sectional view of another embodiment of the blood pump.

FIG. 5 illustrates another embodiment of a layout of the blood pump 100. In this layout, the blood pump 100, the peripheral wall 116 encloses a first internal compartment 117a that surrounds the dividing wall 115 and the blood flow conduit 103. In some embodiments, the first internal compartment 117a can contain the stator 120. The stator 120 can be disposed in the first internal compartment 117a about the dividing wall 115. The removable cap 118 defines a second internal compartment 117b that is located intermediated between the second face 113 and the volute 107 that is in fluid communication with the blood conduit 103 and the outlet opening 105. The second internal compartment 117b can contain the electronics 130 that can be potted within a second potting 151. The placement of the electronics 130 between the volute 107 and the second face 113 creates a heat transfer pathway 170 directly from the electronics 130 into the volute 107 at a thermal zone and to blood transiting through the volute 107. The thermal zone can, in some embodiments, be adjacent to the electronics 130.

In some embodiments, the electronics 130 can be embedded within the second potting 151 and positioned within the second internal compartment 117b such that the electronics are relatively more proximate to the volute 107 than to the second face 113 and/or so that the second potting is thicker between the electronics 130 and the second face 113 than between the electronics 130 and the volute 107. In some embodiments, this greater thickness of the potting between the electronics 130 and the second face 113 than between the electronics 130 and the volute 107 can result in more heat transfer from the electronics to the volute 107 and blood transiting through the volute than to the second face 113. The implanted blood pump 100 can include an electrical connector 172 located proximate to the second face 113 and/or the outlet opening 105. In some embodiments, placement of the electronics 130 as depicted in FIG. 5 can facilitate location of an electrical connector 172 proximate to the second face 113 and/or the outlet opening 105, which placement of the electrical connector 172 can ease implantation of the blood pump 100. Specifically, in some embodiments, placement of the electrical connector 172 proximate to the outlet opening 105 of the blood pump can ease implantation by allowing similar placement of both the cable 119 connecting to the connector 172 and any conduit, tube, or channel connecting to the outlet opening 105 within the patient's body.

The removable cap 118 includes the second face 113, the chamfered edge 114, and defines the outlet opening 105. The cap 118 can be threadably engaged with the peripheral wall 116 to seal the cap 118 in engagement with the peripheral wall 116. The cap 118 includes an inner surface 118a of the cap 118 that defines the volute 107 that is in fluid communication with the outlet opening 105.

In some embodiments, within the internal compartment 117, the electronics 130 are positioned adjacent to the first face 111 and the stator 120 is positioned adjacent to the electronics 130 on an opposite side of the electronics 130 from the first face 111. The electronics 130 include circuit boards 131 and various components 133 carried on the circuit boards 131 to control the operation of the pump 100 by controlling the electrical supply to the stator 120. The housing 110 is configured to receive the circuit boards 131 within the internal compartment 117 generally parallel to the first face 111 for efficient use of the space within the internal compartment 117. The circuit boards also extend radiallyinward towards the dividing wall 115 and radially-outward towards the peripheral wall 116. For example, the internal compartment 117 is generally sized no larger than necessary to accommodate the circuit boards 131, and space for heat dissipation, material expansion, potting materials, and/or other elements used in installing the circuit boards 131. Thus, the external shape of the housing 110 proximate the first face 111 generally fits the shape of the circuits boards 131 closely to provide external dimensions that are not much greater than the dimensions of the circuit boards 131.

Figure 6:
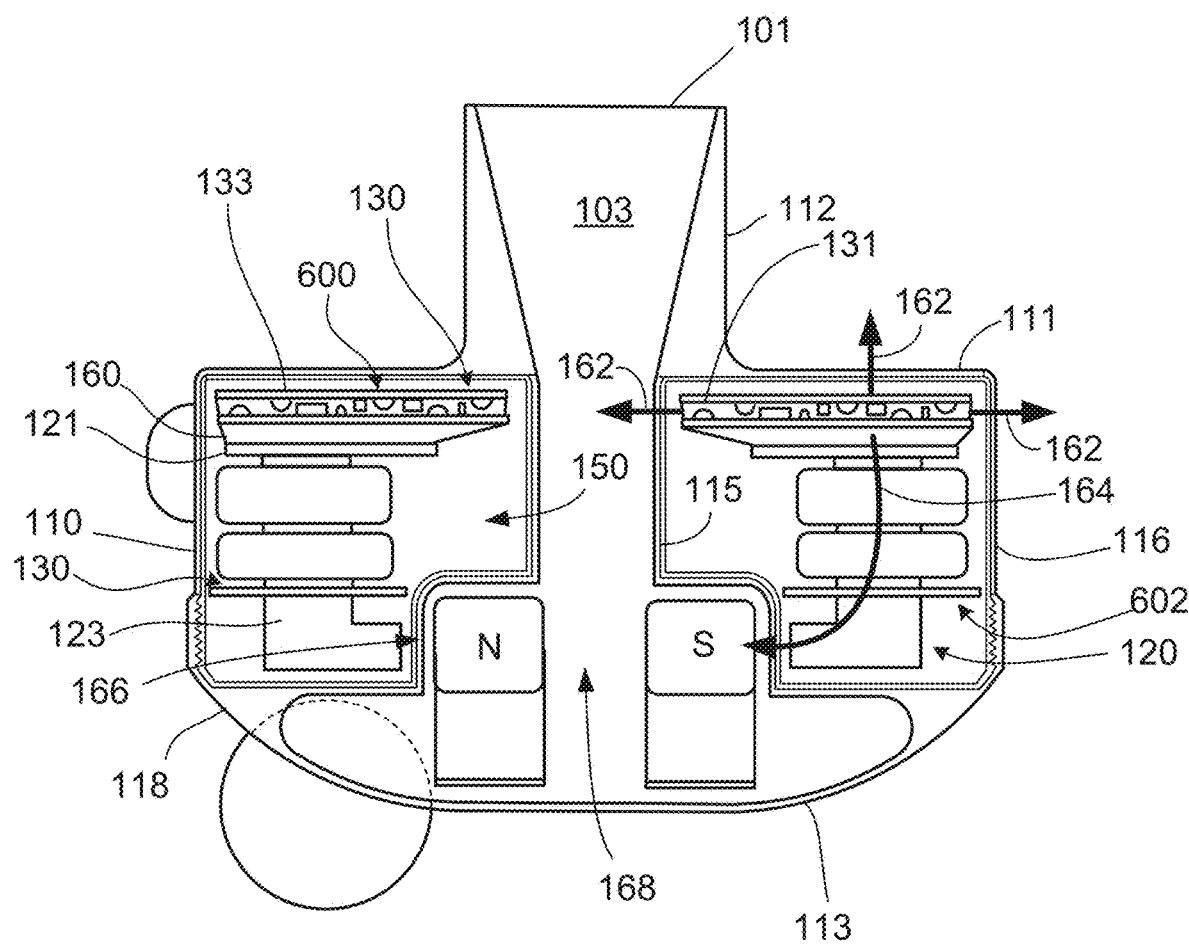
FIG. 6 is a cross-sectional view of an additional embodiment of the blood pump of and conductive heat pathways.

FIG. 6 illustrates another embodiment of a layout of the blood pump 100. In this layout of the blood pump 100 the electronics 130 include first electronics 600 and second electronics 602. In some embodiments, the first electronics 600 can include a first one or several: circuit boards such one or several printed circuit boards; one or several electrical components, or the like; and the second electronics 602 can include a second one or several: circuit boards such one or several printed circuit boards; one or several electrical components, or the like. In some embodiments, the first electronics 600 can be located proximate to the first face 111 and the second electronics 602 can be located between the first electronics 600 and the second face 113. In some embodiments, both the first electronics 600 and the second electronics 602 can be thermally coupled to the stator 120 via the thermal conductor 160, which thermal conductor 160 can be non-electrically conductive.

Figure 7:
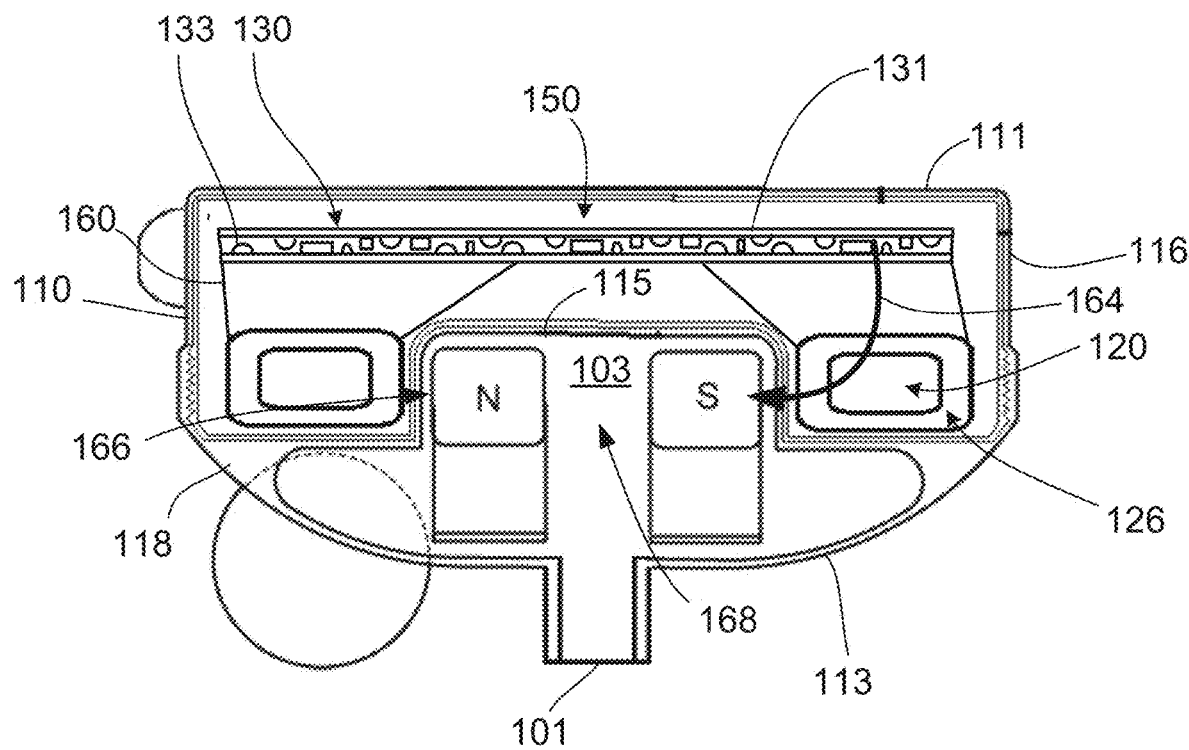
FIG. 7 is a cross-sectional view of an additional embodiment of the blood pump in which the inlet is located proximate to the second face.
Figure 8:
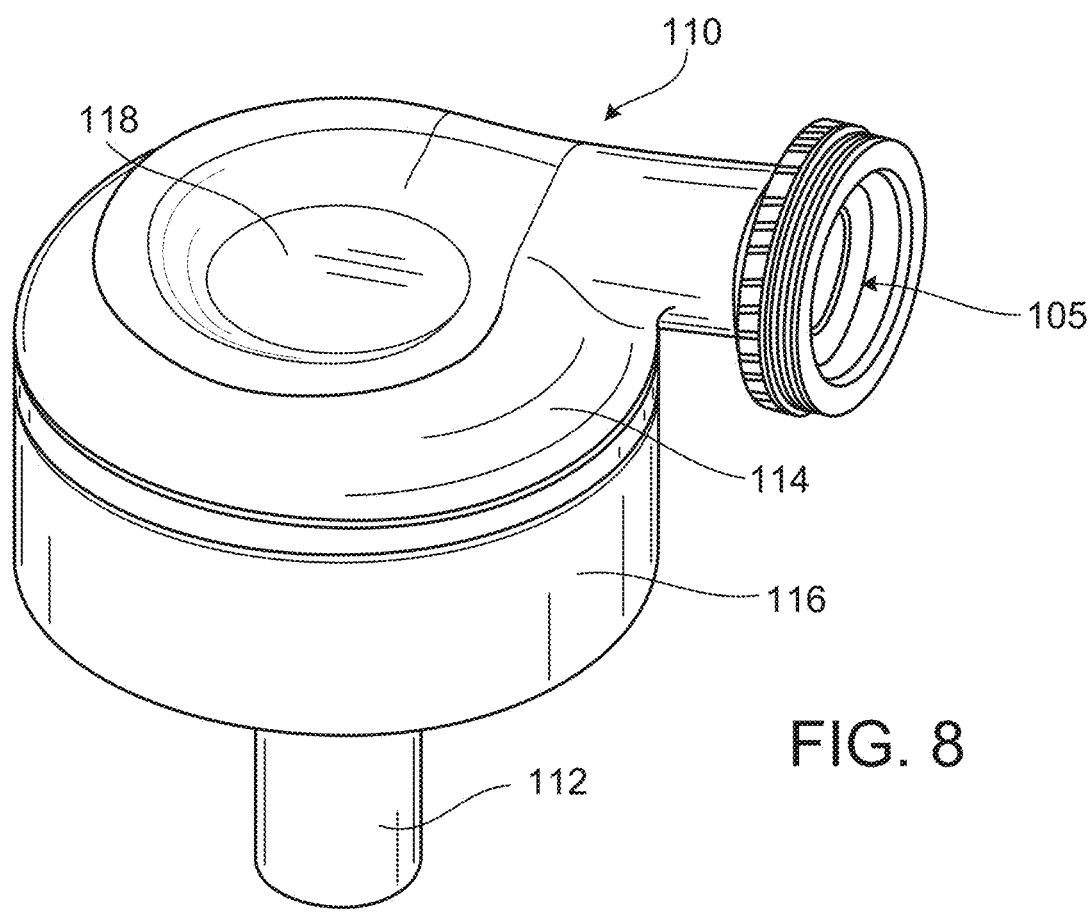
FIG. 8 is a bottom perspective view of a blood pump.
Figure 9:
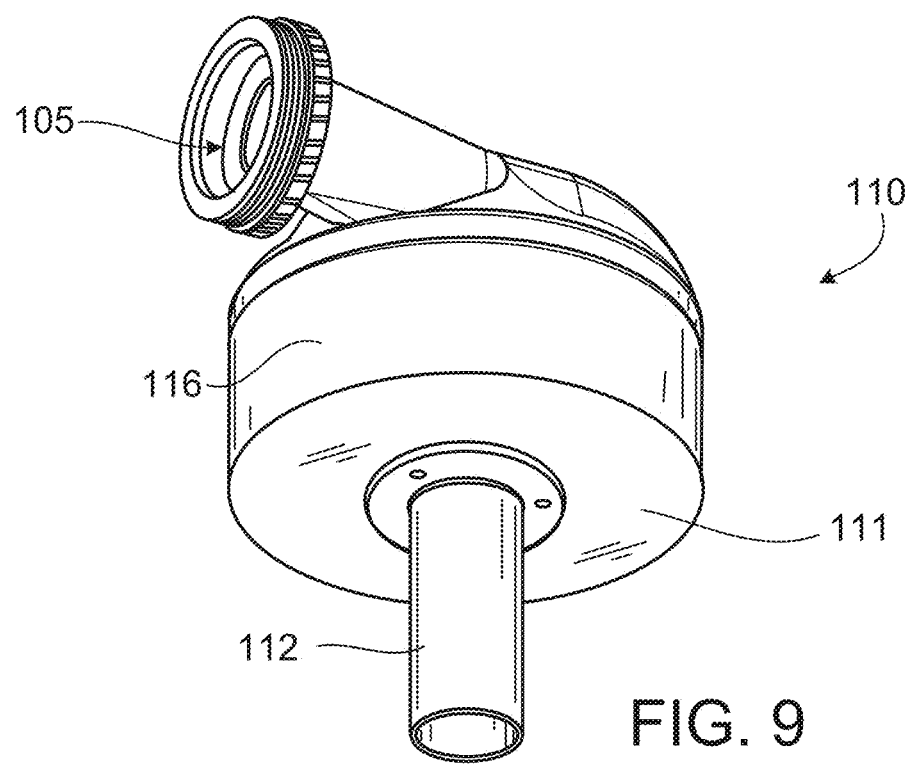
FIG. 9 is a top perspective view of the blood pump of FIG. 8.
Figure 10:
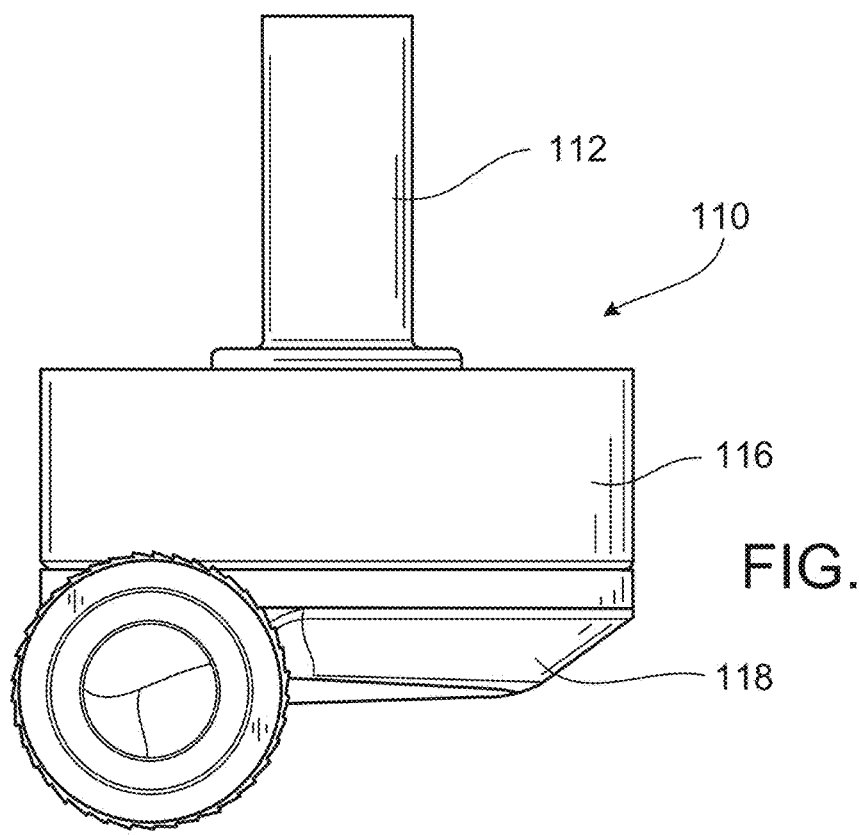
FIG. 10 is a front view of the blood pump of FIG. 8.
Figure 11:
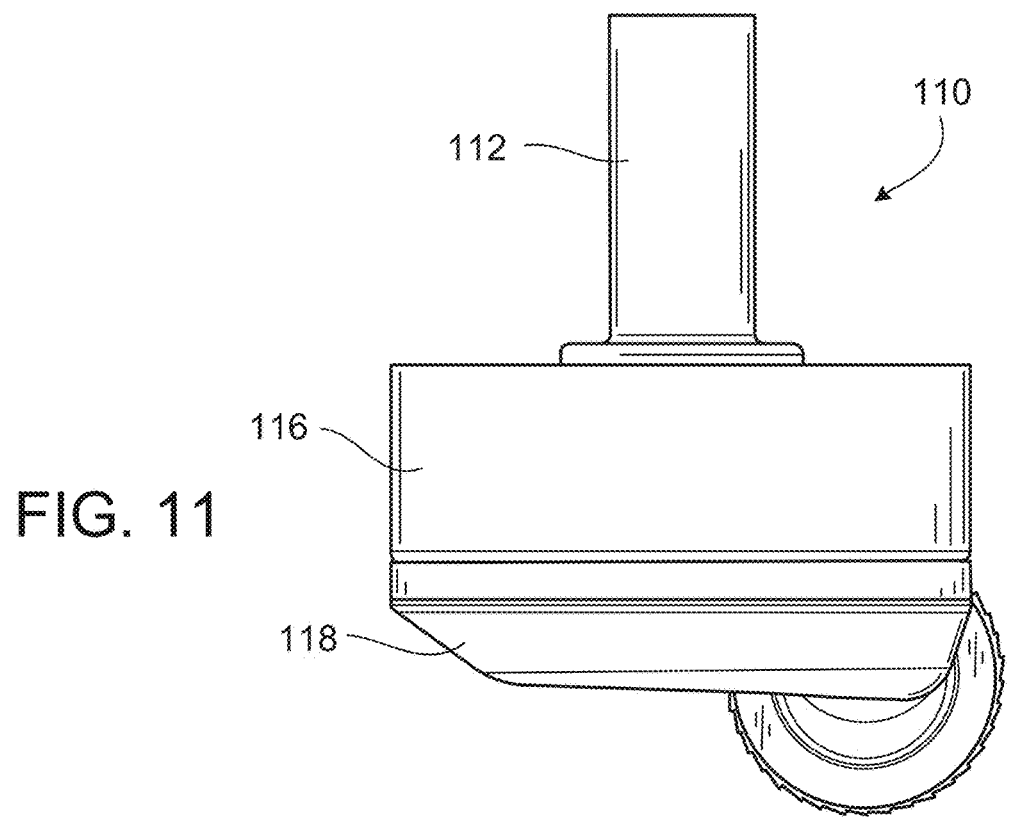
FIG. 11 is a back view of the blood pump of FIG. 8.
Figure 14:
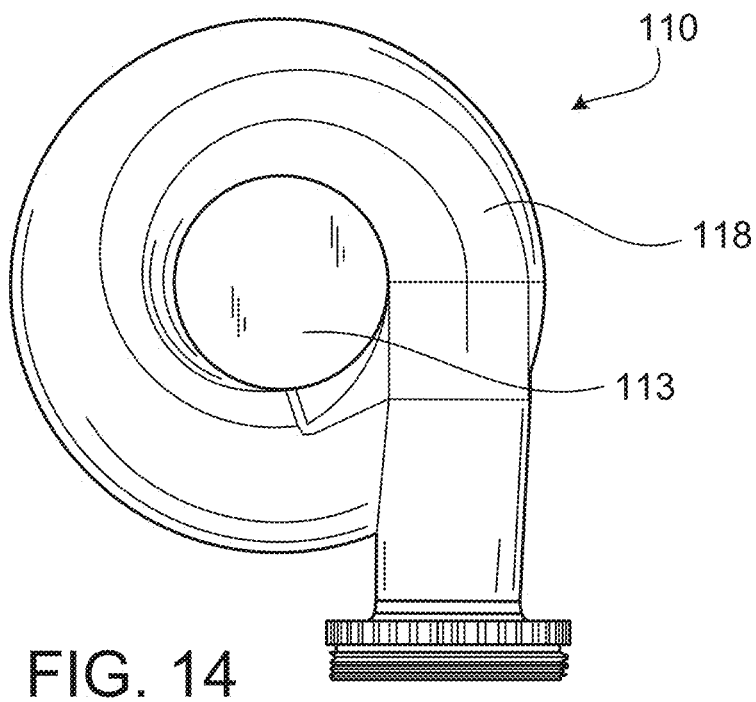
FIG. 14 is a bottom view of the blood pump of FIG. 8.
Figure 15:
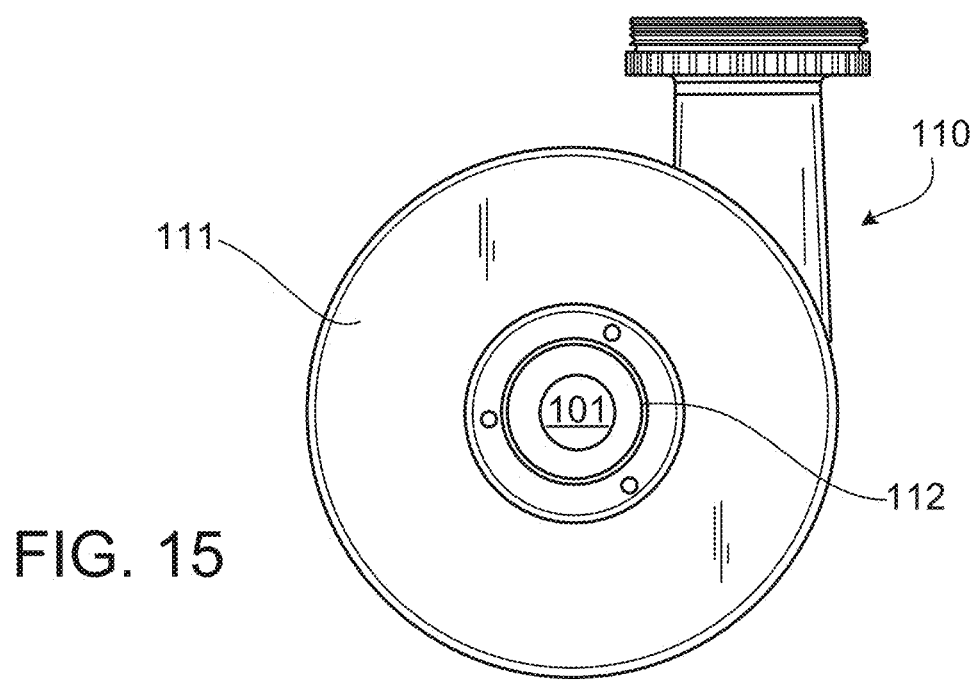
FIG. 15 is a top view of the blood pump of FIG. 8.

FIG. 7 illustrates another embodiment of a layout of the blood pump 100. In this layout of the blood pump 100, the blood flow conduit 103 does not extend from the first face 111 to the second face 113, but rather extends below the volute 107 towards the first face 111. The blood pump 100 includes the stator 120 and the windings 126. As further seen, the windings 126 and stator 120 are thermally connected to the electronics 130 via the thermal conductor 160. In the embodiment of FIG. 7, the blood pump 100 includes the inlet opening 101 located in the second face 113, which inlet opening 101 leads directly into the volute 107. This positioning of the inlet opening 101 in the second face 113 enables the placement of the electronics 130 in closer physical proximity to the blood flow conduit 103 and/or in closer thermal proximity to the blood flow conduit 103. Similar to previously discussed embodiments, in operation, blood is drawn into the blood flow conduit 103 and/or flows through the blood flow conduit 103 and heat is transferred to this blood flowing through the blood flow conduit 104 from the electronics 130 or other components of the blood pump 100, and in some embodiments, via the stator 120.

Figure 3:
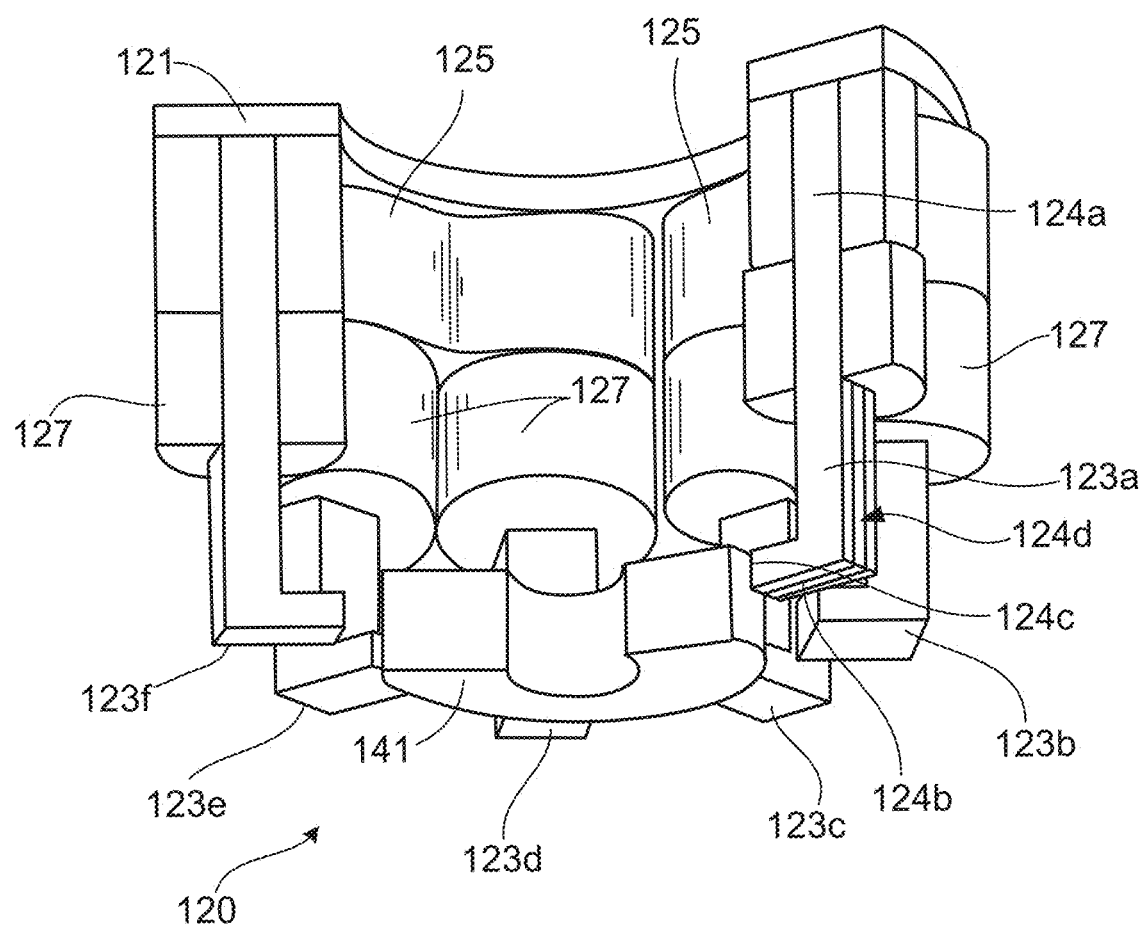
FIG. 3 is a partial cut-away perspective view of a stator of a blood pump.

With continued reference to FIG. 2 and with reference to FIG. 3, the stator 120 includes a back iron 121 and pole pieces 123a-123f arranged at intervals around the dividing wall 115. The back iron 121 extends around the dividing wall 115 and is formed as a generally flat disc of a ferromagnetic material, such as steel, in order to conduct magnetic flux. The back iron 121 can, in some embodiments, be proximate to the control electronics 130. While the back iron 121 can be proximate to the control electronics 130, the back iron 121 is electrically unconnected to the electronics 130. The back iron 121 provides a base for the pole pieces 123a-123f. In some embodiments, the thermal conductor 160 can connect to the stator 120 via the back iron 121 and/or via one or several of the pole pieces 123a-123f.

Each of the pole piece 123a-123f is L-shaped and has a drive coil 125 for generating an electromagnetic field to rotate the rotor 140. For example, the pole piece 123a has a first leg 124a that contacts the back iron 121 and extends from the back iron 121 towards the second face 113. The pole piece 123a also has a second leg 124b that extends from the first leg 124a towards the dividing wall 115 proximate the location of the permanent magnet 141 of the rotor 140. In some embodiments, the second leg 124b terminates at the end 124c proximate to the interior wall 115. The end can be, for example, separated from the interior wall 115 by a distance or a gap of at least: 0.01 millimeters, 0.05 millimeters, 0.1 millimeters, 0.2 millimeters, 0.3 millimeters, 0.4 millimeters, 0.5 millimeters, 1 millimeter, 2 millimeters, 3 millimeters, 4 millimeters, 5 millimeters, between 0 millimeters and 5 millimeters, between 0.05 millimeters and 2.5 millimeters, between 0.05 millimeters and 2 millimeters, between 0.2 millimeters and 1.5 millimeters, between 0.5 millimeters and 1 millimeter, between 1 millimeter and 1.5 millimeters, between 1.5 millimeters and 2 millimeters, between 2 millimeters and 2.5 millimeters, or any other or intermediate distance.

In some embodiments, the second leg 124b, and specifically the end 124c is in thermal connection with a portion of the interior wall 115 proximate to the second leg 124 and can thereby transfer heat to blood transiting the blood flow conduit 103 during operation of the blood pump 100. Each of the pole pieces 123a-123f also has a levitation coil 127 for generating an electromagnetic field to control the radial position of the rotor 140.

Each of the drive coils 125 and the levitation coils 127 includes multiple windings of a conductor around the pole pieces 123a-123f. Particularly, each of the drive coils 125 is wound around two adjacent ones of the pole pieces 123, such as pole pieces 123d and 123e, and each levitation coil 127 is wound around a single pole piece. The drive coils 125 and the levitation coils 127 are wound around the first legs of the pole pieces 123, and magnetic flux generated by passing electrical current though the coils 125 and 127 during use is conducted through the first legs and the second legs of the pole pieces 123 and the back iron 121. The drive coils 125 and the levitation coils 127 of the stator 120 are arranged in opposing pairs and are controlled to drive the rotor and to radially and axially levitate the rotor 140 by generating electromagnetic fields that interact with the permanent magnetic poles S and N of the permanent magnet 141. Because the stator 20 includes both the drive coils 125 and the levitation coils 127, only a single stator is needed to levitate the rotor 140 using only passive and active magnetic forces. The permanent magnet 141 in this configuration has only one magnetic moment and is formed from a monolithic permanent magnetic body 141. For example, the stator 120 can be controlled as discussed in U.S. Pat. No. 6,351,048, the entire contents of which are incorporated herein by reference for all purposes. The control electronics 130 and the stator 120 receive electrical power from a remote power supply via a cable 119 (FIG. 1).

The rotor 140 is arranged within the housing 110 such that its permanent magnet 141 is located upstream of impeller blades in a location closer to the inlet opening 101. The permanent magnet 141 is received within the blood flow conduit 103 proximate the second legs 124b of the pole pieces 123 to provide the passive axial centering force though interaction of the permanent magnet 141 and ferromagnetic material of the pole pieces 123. The permanent magnet 141 of the rotor 140 and the dividing wall 115 form a gap 108 between the permanent magnet 141 and the dividing wall 115 when the rotor 140 is centered within the dividing wall 115. In some embodiments, the thermal zone 168 is located adjacent the gap 108 such that the gap is between the permanent magnet 141 and the portion 166 of the dividing wall 115. The gap 108 may be from about 0.2 millimeters to about 2 millimeters. For example, the gap 108 is approximately 1 millimeter. The north permanent magnetic pole N and the south permanent magnetic pole S of the permanent magnet 141 provide a permanent magnetic attractive force between the rotor 140 and the stator 120 that acts as a passive axial centering force that tends to maintain the rotor 140 generally centered within the stator 120 and tends to resist the rotor 140 from moving towards the first face 111 or towards the second face 113. When the gap 108 is smaller, the magnetic attractive force between the permanent magnet 141 and the stator 120 is greater, and the gap 108 is sized to allow the permanent magnet 141 to provide the passive magnetic axial centering force having a magnitude that is adequate to limit the rotor 140 from contacting the dividing wall 115 or the inner surface 118a of the cap 118. The rotor 140 also includes a shroud 145 that covers the ends of the impeller blades 143 facing the second face 113 that assists in directing blood flow into the volute 107. The shroud 145 and the inner surface 118a of the cap 118 form a gap 109 between the shroud 145 and the inner surface 118a when the rotor 140 is levitated by the stator 120. The gap 109 is from about 0.2 millimeters to about 2 millimeters. For example, the gap 109 is approximately 1 millimeter.

As blood flows through the blood flow conduit 103, blood flows through a central aperture 141a formed through the permanent magnet 141. Blood also flows through the gap 108 between the rotor 140 and the dividing wall 115 and through the gap 109 between the shroud 145 and the inner surface 108a of the cap 118. During operation the gaps 108 and 109 are large enough to allow adequate blood flow to limit clot formation that may occur if the blood is allowed to become stagnant. The gaps 108 and 109 are also large enough to limit pressure forces on the blood cells such that the blood is not damaged when flowing through the pump 100.

Because the rotor 140 is radially suspended by active control of the levitation coils 127 as discussed above, and because the rotor 140 is axially suspended by passive interaction of the permanent magnet 141 and the stator 120, no rotor levitation components are needed proximate the second face 113. The incorporation of all the components for rotor levitation in the stator 120 (i.e., the levitation coils 127 and the pole pieces 123) allows the cap 118 to be contoured to the shape of the impeller blades 143 and the volute 107. Additionally, incorporation of the rotor levitation components in the stator 120 eliminates the need for electrical connectors extending from the compartment 117 to the cap 118, which allows the cap to be easily installed and/or removed and eliminates potential sources of pump failure.

In use, and with reference to the embodiment of FIGS. 2 and 4, the drive coils 125 of the stator 120 generates electromagnetic fields through the pole pieces 123 that selectively attract and repel the magnetic north pole N and the magnetic south pole S of the rotor 140 to cause the rotor 140 to rotate within stator 120. As the rotor 140 rotates, the impeller blades 143 force blood into the volute 107 such that blood is forced out of the outlet opening 105. Additionally, the rotor draws blood into pump 100 through the inlet opening 101. As blood is drawn into the blood pump by rotation of the impeller blades 143 of the rotor 140, the blood flows through the inlet opening 101 and flows through the control electronics 130 and the stator 120 toward the rotor 140. As the blood passes through the control electronics 130 and the stator 120, the blood passes through the thermal zone 168 defined by the portion 166 of the interior wall 115 that is heated by the second conductive heat transfer pathway 164. Heat transfers from the electronics 130 into the blood in the thermal zone 168. Blood flows through the aperture 141a of the permanent magnet 141 and between the impeller blades 143, the shroud 145, and the permanent magnet 141, and into the volute 107. Blood also flows around the rotor 140, through the gap 108 and through the gap 109 between the shroud 145 and the inner surface 118a of the cap 118. The blood exits the volute 107 through the outlet opening 105.

In use, and with reference to the embodiment of FIG. 5, the drive coils 125 of the stator 120 generates electromagnetic fields through the pole pieces 123 that selectively attract and repel the magnetic north pole N and the magnetic south pole S of the rotor 140 to cause the rotor 140 to rotate within stator 120. As the rotor 140 rotates, the impeller blades 143 force blood into the volute 107 such that blood is forced out of the outlet opening 105. Additionally, the rotor draws blood into pump 100 through the inlet opening 101. As blood is drawn into the blood pump by rotation of the impeller blades 143 of the rotor 140, the blood flows through the inlet opening 101 and flows through the stator 120 toward the rotor 140. Blood flows through the aperture 141a of the permanent magnet 141 and between the impeller blades 143, the shroud 145, and the permanent magnet 141, and into the volute 107. While in the volute 107, the blood flows between the stator 120 and the electronics 130, which electronics 130 are positioned between the volute 107 and the second face 113. Heat transfers from the electronics 130 into the blood in the volute 107. Blood also flows around the rotor 140, through the gap 108 and through the gap 109 between the shroud 145 and the inner surface 118a of the cap 118. The blood exits the volute 107 through the outlet opening 105.

A number of implementations have been described. Nevertheless, it will be understood that various modifications may be made without departing from the spirit and scope of the claimed invention. For example, the cap 118 can be engaged with the peripheral wall 116 using a different attachment mechanism or technique, such as snap-fit engagement, adhesives, and/or welding. Additionally, while the cap 118 has been described as defining the outlet opening 105 and the chamfered edge 114, the outlet opening 105 and/or the chamfered edge 114 can be defined by the peripheral wall 116 or by both the peripheral wall 116 and the cap 118. Similarly, the dividing wall 115 can be formed as part of the cap 118.

Additionally, the rotor 140 can include two or more permanent magnets. The number and configuration of the pole pieces 123 can also be varied. The operation of the control electronics 130 is selected to account for the number and position of pole pieces of the stator and permanent magnets of the rotor. Also, the cap 118 can be engaged with the peripheral wall using other techniques, such as adhesives, welding, snap-fit, shrink-fit, or other technique or structure.

Similarly, the first face 111 may be formed from a separate piece of material than the peripheral wall 116 and the first face 111, including the inlet cannula 112, can be attached to the peripheral wall 116, such as by welding, after the control electronics 130 and the stator 120 have been mounted in the internal compartment 117. The shroud 145 may be omitted and optionally replaced by other flow control devices to achieve a desired pump efficiency. As another option, the control electronics 130 can be located external to the pump 100, such as in a separate housing implanted in the patient's abdomen, or external to the patient's body.

In some implementations, the dimensions of the housing 110 can be larger or smaller than those described above.

Similarly, the ratio of the width W of the housing 110 to the thickness T of the housing can be different than the ratio described above. For example, the width W can be from about 1.1 to about 5 times greater than the thickness T. Additionally, the permanent magnet 141 of the rotor 140 can include two or more pairs of north and south magnetic poles. While the peripheral wall 116 and the dividing wall 115 are illustrated as cylinders having circular cross-sectional shapes, one or both can alternatively be formed having other cross-sectional shapes, such as oval, or an irregular shape. Similarly, the peripheral wall 116 can be tapered such that the housing does not have a constant width W from the first face 111 to the second face 113.

As mentioned above, in some implementations, the blood pump 100 can be used to assist a patient's heart during a transition period, such as during a recovery from illness and/or surgery or other treatment. In other implementations, the blood pump 100 can be used to partially or completely replace the function of the patient's heart on a generally permanent basis, such as where the patient's aortic valve is surgically sealed.

Figure 16:
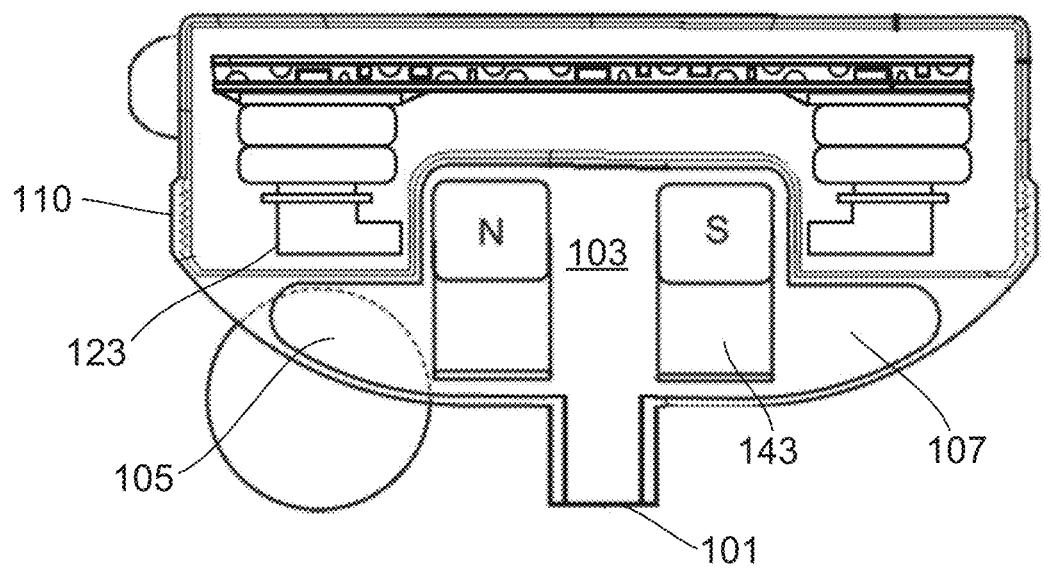
FIG. 16 is a cross-section view of an additional embodiment of the blood pump including L-shaped pole pieces and in which the inlet is located proximate to the second face.

FIG. 16 illustrates another embodiment of a layout of the blood pump 100. The layout of the blood pump 100 in FIG. 16 is similar to the layout of the blood pump 100 in FIG. 7, with the exception that the blood pump 100 in FIG. 16 includes the pole pieces 123a-123f and windings 126 similar to those shown in FIG. 2, and windings 126 that can include, for example, a drive coil 125 and a levitation coil 127.

Figure 17:
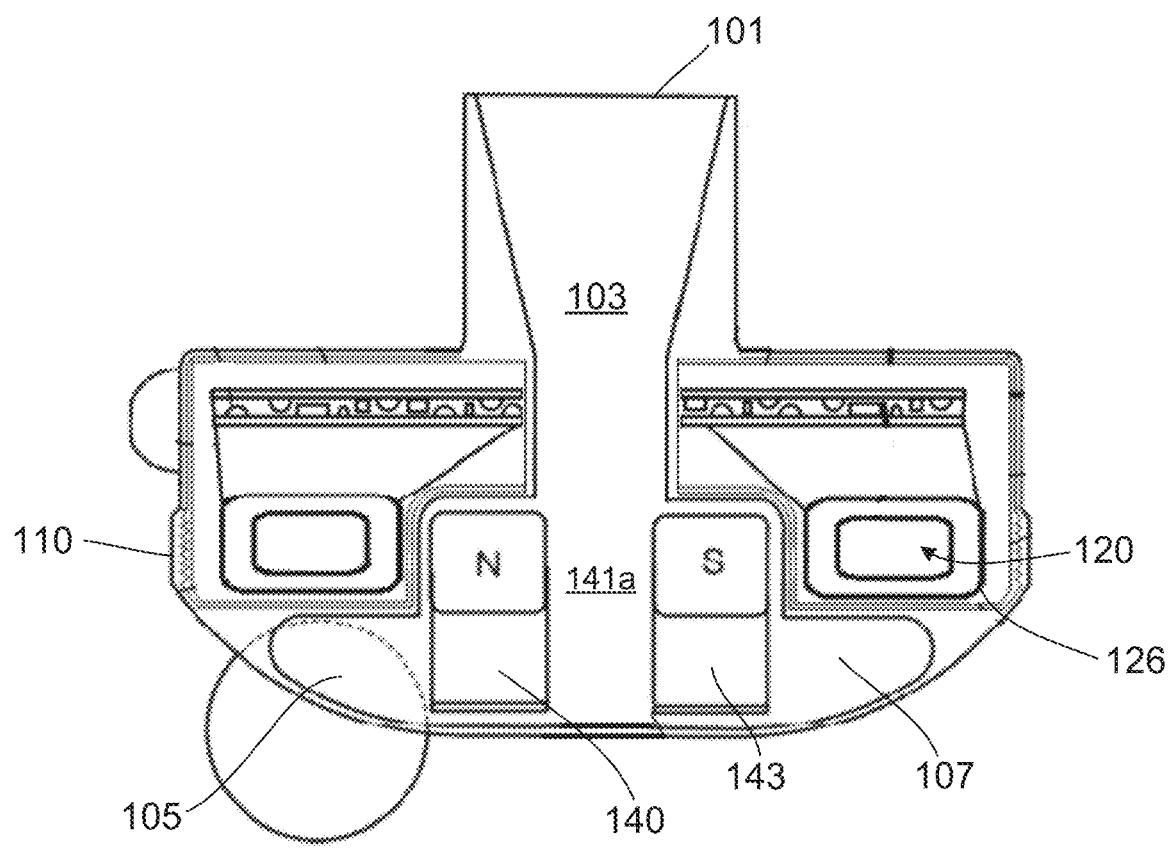
FIG. 17 is a cross-section view of an additional embodiment of the blood pump in which windings are positioned adjacent to a permanent magnet located on a rotor of the blood pump.

FIG. 17 illustrates another embodiment of a layout of the blood pump 100. The layout of the blood pump 100 in FIG. 17 is similar to the layout of the blood pump 100 in FIG. 2, with the exception that the blood pump 100 in FIG. 17 does not include L-shaped pole pieces 123a-123f, but rather includes the stator 120 and the windings 126 configured so the windings 126 are positioned adjacent to the permanent magnet 141 attached to the rotor 140.

Other variations are within the spirit of the present invention. Thus, while the invention is susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions, and equivalents falling within the spirit and scope of the invention, as defined in the appended claims.

In the preceding description, various embodiments of the present invention are described. For purposes of explanation, specific configurations and details are set forth in order to provide a thorough understanding of the embodiments. However, it will also be apparent to one skilled in the art that the present invention may be practiced without the specific details. Furthermore, well-known features may be omitted or simplified in order not to obscure the embodiment being described.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

All references, including publications, patent applications, and patents, cited herein are hereby incorporated by reference to the same extent as if each reference were individually and specifically indicated to be incorporated by reference and were set forth in its entirety herein.

What is claimed is:

1. An implantable blood pump comprising:
    a pump housing comprising a blood flow conduit extending through the pump housing and an internal volume;
    a rotor comprising a magnet and disposed within the blood flow conduit;
    a magnetic core disposed in the internal volume and circumferentially surrounding the blood flow conduit and the rotor, wherein the magnetic core has an central aperture through which the blood flow conduit extends so that a blood flow flowing through the blood flow conduit passes through the central aperture;
    a controller disposed in the internal volume; and
    a thermal conductor connected to and between the controller and the magnetic core, wherein the thermal conductor and the magnetic core form at least a portion of a continuous thermal pathway between the controller and the blood flow conduit, and wherein the continuous thermal pathway is configured to transfer heat from the controller to blood transiting the blood flow conduit.

2. The implantable blood pump of claim 1, wherein the thermal conductor provides a path of least resistance for flow of heat generated by the controller to the blood flow flowing through the blood flow conduit, and wherein the thermal conductor comprises a thermal interface material.

3. The implantable blood pump of claim 2, wherein the thermal interface material comprises a thermal conductive pad or thermal grease.

4. The implantable blood pump of claim 1, wherein the magnetic core is thermally coupled to blood transiting the blood flow conduit via the blood flow conduit.

5. The implantable blood pump of claim 1, wherein the blood flow conduit comprises a blood flow inlet and a blood flow exit, and wherein the controller is positioned relatively proximate to the blood flow inlet than the magnetic core.

6. The implantable blood pump of claim 5, wherein the magnetic core comprises a plurality of L-shaped pole pieces that circumferentially surround the blood flow conduit.

7. The implantable blood pump of claim 1, wherein the thermal conductor is electrically non-conductive.

8. The implantable blood pump of claim 1, wherein the magnetic core comprises a plurality of pole pieces that circumferentially surround the blood flow conduit.

9. The implantable blood pump of claim 8, wherein each of the pole pieces comprises a first leg extending along the blood flow conduit and a second leg that extends towards the blood flow conduit.

10. The implantable blood pump of claim 9, wherein an end of each of the second legs is separated from the blood flow conduit by a gap of between 0.05 mm and 2 mm.

11. The implantable blood pump of claim 8, wherein the thermal conductor contacts at least one of the pole pieces.

12. The implantable blood pump of claim 8, wherein the magnetic core comprises a back iron, and wherein the thermal conductor contacts the back iron.

13. An implantable blood pump comprising:
a pump housing comprising an exterior wall and an interior wall, wherein the exterior wall and the interior wall together define an internal volume, and wherein the interior wall defines a blood flow conduit extending through the pump housing;
a rotor comprising a magnet and disposed within the blood flow conduit;
a magnetic core disposed in the internal volume and circumferentially surrounding the blood flow conduit and the rotor, wherein the magnetic core has an central aperture through which the blood flow conduit extends so that a blood flow flowing through the blood flow conduit passes through the central aperture;
a controller disposed in the internal volume;
a first conductive heat transfer pathway thermally coupling the controller with the exterior wall and the interior wall; and
a second conductive heat transfer pathway with a thermal conductor connected to and between the controller and the magnetic core, wherein the second conductive heat transfer pathway thermally couples the controller with a portion of the interior wall.

* * * * *